United States Patent
Miller et al.

(10) Patent No.: US 9,868,686 B2
(45) Date of Patent: Jan. 16, 2018

(54) HYDROFORMYLATION PROCESS

(71) Applicant: Dow Technology Investments LLC, Midland, MI (US)

(72) Inventors: Glenn A. Miller, South Charleston, WV (US); Victoria L. Biedenstein, Eden Prairie, MN (US); Atul Manilal Shah, London (GB); Martin Lucas Smidt, London (GB); David Keith Welch, London (GB)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 15/444,827

(22) Filed: Feb. 28, 2017

(65) Prior Publication Data
US 2017/0253549 A1   Sep. 7, 2017

Related U.S. Application Data

(60) Provisional application No. 62/301,792, filed on Mar. 1, 2016.

(51) Int. Cl.
*C07C 45/50*   (2006.01)
*B01D 19/00*   (2006.01)

(52) U.S. Cl.
CPC ........ *C07C 45/505* (2013.01); *B01D 19/0042* (2013.01); *B01D 19/0063* (2013.01)

(58) Field of Classification Search
CPC .... C07C 45/50; C07C 45/505; B01D 19/0042
See application file for complete search history.

(56) References Cited

U.S. PATENT DOCUMENTS

| | | |
|---|---|---|
| 3,527,809 A | 9/1970 | Pruett et al. |
| 4,148,830 A | 4/1979 | Pruett et al. |
| 4,166,773 A | 9/1979 | Higley et al. |
| 4,277,627 A | 7/1981 | Bryant et al. |
| 5,288,918 A | 2/1994 | Maher et al. |
| 6,500,991 B2 | 12/2002 | Wiese et al. |
| 6,946,580 B2 | 9/2005 | Banister et al. |
| 8,404,903 B2 | 3/2013 | Cox et al. |
| 2004/0138508 A1 | 7/2004 | Tinge et al. |

*Primary Examiner* — Sikarl Witherspoon

(57) ABSTRACT

The present invention relates generally to hydroformylation processes. In one embodiment, a process of the present invention comprises: (a) contacting CO, $H_2$, and at least one olefin under hydroformylation conditions sufficient to form at least one aldehyde product in the presence of a hydroformylation catalyst; (b) removing a product-containing liquid from the reaction zone and sending it to a vaporizer, which comprises a vaporizing zone and a vapor/liquid separation zone, wherein the product-containing liquid, which comprises crude product and catalyst, is heated in the vaporizing zone to form a mixture of gas and catalyst-containing liquid, which mixture is then phase separated in the separation zone, which separation zone has a liquid withdrawal port, a liquid region, a vapor space and a gas-liquid interface, wherein the liquid region comprises at least one divider plate, which optionally contains at least one perforation, wherein at least a portion of at least one divider plate is in proximity to the gas-liquid interface, with the proviso that at least a portion of at least one divider plate is at or below the interface, and wherein the temperature of the catalyst-containing liquid, measured at the liquid withdrawal port, is lower than the temperature of the vapor space.

11 Claims, 3 Drawing Sheets

HYDROFORMYLATION PROCESS

BACKGROUND OF THE INVENTION

The invention relates to a hydroformylation process.

Methods for producing aldehydes by the hydroformylation of an olefinically unsaturated organic compound with carbon monoxide and hydrogen in the presence of a rhodium-phosphorus complex catalyst and free phosphorus ligand are well known in the art, as evidenced by the low pressure oxo hydroformylation process of U.S. Pat. No. 3,527,809 and the rhodium catalyzed liquid recycle hydroformylation process of U.S. Pat. No. 4,148,830.

U.S. Pat. No. 3,527,809 discloses a hydroformylation process wherein olefinically unsaturated organic compounds are hydroformylated with carbon monoxide and hydrogen in the presence of a rhodium-phosphorus complex catalyst and free phosphorus ligand to produce aldehydes in high yields at low temperatures and low pressures. It is known that under such hydroformylation conditions, some of the product aldehydes undergo a condensation reaction to form higher-boiling, i.e., heavy, aldehyde condensation by-products, such as dimers, trimers and tetramers.

U.S. Pat. No. 4,148,830 discloses the use of these higher-boiling liquid aldehyde condensation by-products as a reaction solvent for the catalyst, which solvent also makes an excellent carrier for a continuous liquid recycle process. A continuous process removes from the reactor a liquid reaction effluent stream, which comprises the product, the solubilized catalyst, free phosphorus ligand and the higher-boiling aldehyde condensation by-products. The aldehyde product is then separated from the product solution by rapid volatilization in a vaporizer. The volatilized aldehyde product and the non-volatilized catalyst-containing liquid reaction solution is then disengaged in a gas-liquid separator, wherein the vaporized aldehyde product vapor stream is passed overhead through a condenser for recovery and the remaining non-volatilized catalyst containing liquid reaction solution is removed and recycled back to the reaction zone. A consideration in the design and operation of the vaporizer is the need to balance the rate of removal of the heavy condensation by-products, or heavies, with their rate of formation. If the heavies build up too much, the useful capacity and effectiveness of the hydroformylation system becomes reduced and the catalyst has to be replaced. This issue is reviewed in CN100522912.

Due to the sensitive nature of many ligands, the operation of the vaporizer must be designed to minimize time at elevated temperature. For example, in U.S. Pat. No. 4,166,773, it is preferred that the contact time at vaporizer temperatures be minimized, e.g., preferably less than 20 seconds. CN 1227190C teaches that the entire contact time in the vaporizer (including the heated tubes, cyclone, and gas-liquid separation section) should be less than 15 minutes.

An overly aggressive vaporizer operation can result in the loss of phosphorus ligand during the process due to the presence of volatilized phosphorus ligand in the vaporized aldehyde product. There is an economic penalty associated with heavies build-up and/or physical loss of the ligand. These problems can also lead to a need for further processing of the crude aldehyde product if deactivation of downstream aldehyde hydrogenation catalysts, which are employed in producing alcohols from the aldehyde, is to be prevented or at least minimized.

In a conventional, prior art vaporizer, such as the one shown in FIGS. 1a and 1b, the reaction fluid from the hydroformylation reaction zone is fed by stream (1) to the vaporizing zone (2) where the fluid is heated and the volatiles enter the gas phase, thus forming a mixture of gas and liquid phase materials. At the bottom of the vaporizing zone, this gas-liquid mixture enters the gas-liquid separation zone (3) where the volatile gases are separated from the non-volatilized material. The gases exit the gas-liquid separation zone via stream (4) through optional demisters (not shown), and other means to prevent entrainment of non-volatile materials, and are then cooled and collected downstream for further purification (not shown). The non-volatilized material is cooled by heat exchanger (6) and the cooled non-volatile material exits via stream (5) for further processing or to be returned directly to the reaction zone. In FIG. 1b, the heat exchange occurs in an external loop such that the non-volatile material is collected in the bottom of the gas-liquid separation zone. The liquid level, or gas-liquid interface level, (11) is maintained by varying the flows of streams (5a) and (5b). The liquid exits via stream (5) to the suction side of a pump (9), then is sent through a cooler (6) and is sent back to the reaction zone or to subsequent processing equipment (not shown) via stream (5b). A fraction of the cooled liquid can be returned to the gas-liquid separation zone via recycle stream (5a). Returning cooled liquid to the liquid region of the gas-liquid separation zone results in a lower temperature for the liquid region.

It is desirable to cool the non-volatile material in zone (3) as fast as possible since hydroformylation catalysts, especially phosphites and many phosphines, are thermally sensitive.

Unfortunately, this design results in a cold zone at the bottom of the gas-liquid separation zone (3). Thus, the desired product may condense at the gas-liquid interface (11) rather than escape the separation zone via stream (4). This results in a loss of efficiency as well as the buildup of aldehyde heavies (the least volatile material in the system). The cooled non-volatilized material in the separation zone may contain convection currents, which bring up cool fluid to the surface, thus cooling the gas liquid interface and exacerbating the problem.

It would be desirable to have a low-cost process wherein the catalyst-containing, non-volatile liquid material is quickly cooled without also condensing substantial amounts of the gaseous product stream.

SUMMARY

In one aspect, the process of the invention is such a process and comprises: (a) contacting CO, $H_2$, and at least one olefin under hydroformylation conditions sufficient to form at least one aldehyde product in the presence of a hydroformylation catalyst; (b) removing a product-containing liquid from the reaction zone and sending it to a vaporizer, which comprises a vaporizing zone and a vapor/liquid separation zone, wherein the product-containing liquid, which comprises crude product and catalyst, is heated in the vaporizing zone to form a mixture of gas and catalyst-containing liquid, which mixture is then phase separated in the separation zone, which separation zone has a liquid withdrawal port, a liquid region, a vapor space and a gas-liquid interface, wherein the liquid region comprises at least one divider plate, which optionally contains at least one perforation, wherein at least a portion of at least one divider plate is in proximity to the gas-liquid interface, with the proviso that at least a portion of at least one divider plate is at or below the interface, and wherein the temperature of the catalyst-containing liquid, measured at the liquid withdrawal port, is lower than the temperature of the vapor space.

Surprisingly, the simple hardware employed in the process of the invention results in improved heavies removal, reduced exposure of the catalyst to elevated temperatures, and lower rates of catalyst degradation.

BRIEF DESCRIPTION OF THE DRAWINGS

FIG. 5a represents a "straight sheath" design while FIGS. 5b and 5c represent "wrap-around sheath" designs wherein the sheath at least partially encloses the cooling bundle, e.g., in a circular or cylindrical way, such that the liquid is guided over the bundle tubes to enable maximum efficiency of the cooler. FIG. 5a includes a top-down view showing that a slot or opening is created between 2 plates.

FIG. 7b shows a chimney (12) which allows gas to collect under the cone.

DETAILED DESCRIPTION

Figure 1A:
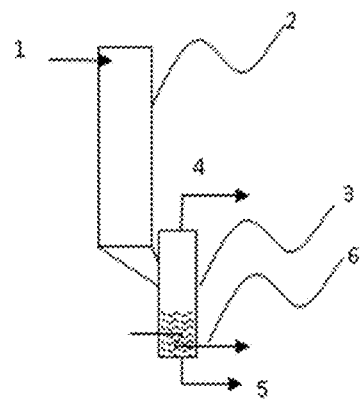
FIGS. 1a and 1b show cross-sectional schematics of prior art vaporizer designs.
Figure 1B:
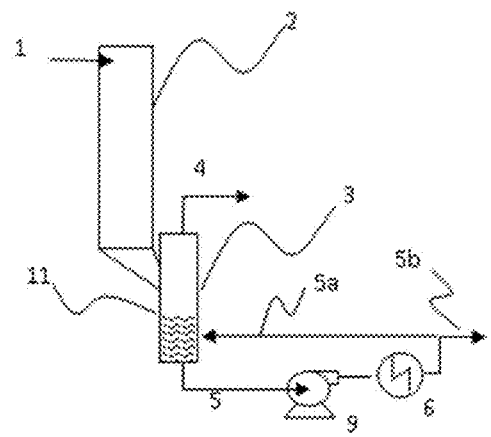

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

The term "vaporizer" refers to a device that comprises a vaporizing zone and a separation zone, wherein product-containing liquid, which comprises crude product and catalyst, is heated in the vaporizing zone to form a mixture of gas and catalyst-containing liquid, which is then phase separated in the separation zone.

As used herein, the term "perforation" means a hole or opening. In some embodiments of the invention, an opening may be formed by a combination of plates; see, e.g., FIGS. 5a-c.

Unless stated to the contrary, or implicit from the context, all parts and percentages are based on weight and all test methods are current as of the filing date of this application.

The hydroformylation portion of the process of the invention employs conventional hydroformylation conditions and raw materials, e.g., hydrogen, CO, at least one olefin, and a catalyst.

The process of the invention employs a vaporizer comprising a separation zone. This zone advantageously provides focused contact between an input liquid and a cooling heat exchanger.

In one embodiment, a process of the present invention comprises: (a) contacting CO, $H_2$, and at least one olefin under hydroformylation conditions sufficient to form at least one aldehyde product in the presence of a hydroformylation catalyst; (b) removing a product-containing liquid from the reaction zone and sending it to a vaporizer, which comprises a vaporizing zone and a vapor/liquid separation zone, wherein the product-containing liquid, which comprises crude product and catalyst, is heated in the vaporizing zone to form a mixture of gas and catalyst-containing liquid, which mixture is then phase separated in the separation zone, which separation zone has a liquid withdrawal port, a liquid region, a vapor space and a gas-liquid interface, wherein the liquid region comprises at least one divider plate, which optionally contains at least one perforation, wherein at least a portion of at least one divider plate is in proximity to the gas-liquid interface, with the proviso that at least a portion of at least one divider plate is at or below the interface, and wherein the temperature of the catalyst-containing liquid, measured at the liquid withdrawal port, is lower than the temperature of the vapor space.

In some embodiments, at least one plate is perforated. At least one plate, in some embodiments, is sloped to direct the non-volatilized catalyst-containing liquid, towards at least one perforation.

In some embodiments, a heat exchanger controls the temperature of the catalyst-containing liquid in at least a portion of the liquid region. The heat exchanger, in some such embodiments, is in the liquid region, and at least two plates define an opening directly above the heat exchanger. In some such embodiments, the opening above the heat exchanger is a first opening, and the plates further define a second opening below the heat exchanger, the second opening having the same or greater area as the first opening.

In some embodiments, at least one divider plate at least partially encloses the heat exchanger.

In some embodiments where the liquid region contains the heat exchanger, at least one plate comprises at least one perforation that is directly above the heat exchanger.

The catalyst, in some embodiments, comprises a rhodium-phosphorus complex catalyst and the product is a $C_3$-$C_{20}$ aldehyde.

In some embodiments, a non-condensable gas flow is introduced below at least one plate such that a gas bubble or zone is maintained under the plate.

In some embodiments, at least one plate reduces heat transfer between the vapor space and the liquid region.

The process comprise a combination of two or more embodiments as described herein.

Figure 2:
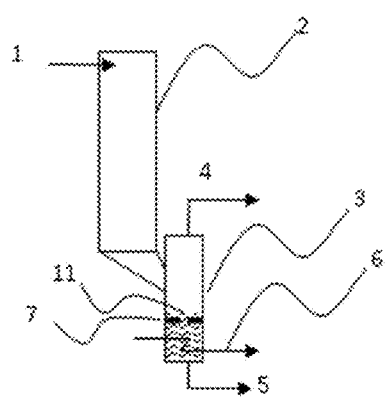
FIG. 2 is a cross-sectional schematic of a vaporizer with a horizontal divider plate just below the gas-liquid interface in the vaporizer gas-liquid separation zone.

As shown in FIG. 2, a divider plate (7) separates the bulk of the liquid from the upper gas phase, reducing or minimizing the condensation of vapor into the cooled liquid below the plate. Divider plate (7) is formed from two plates that define an opening or perforation. Divider plate (7) with a portion just below the liquid level (11) results in a dual-temperature zone within the body (3) of the gas-liquid separation zone. The plate prevents the convection current effect and generates a small quiescent zone, or boundary layer, on both sides of the plate. This zone or layer insulates the bulk of the liquid region from the vapor space. The heat transfer from the vapor space to the liquid region is inefficient; therefore, the liquid in contact with the gaseous phase remains relatively hot, thus minimizing condensation. The volume of the quiescent zone material is small and this material is constantly in flow towards the bottom of the vessel, thus the time this solution is exposed to elevated temperature is minimized.

The material under the plate is relatively cooler and, while it may comprise a larger volume than the top liquid layer, the total time at elevated temperature is lower, so that the net amount of observed side reactions is lower than that of the prior art.

Figure 3:
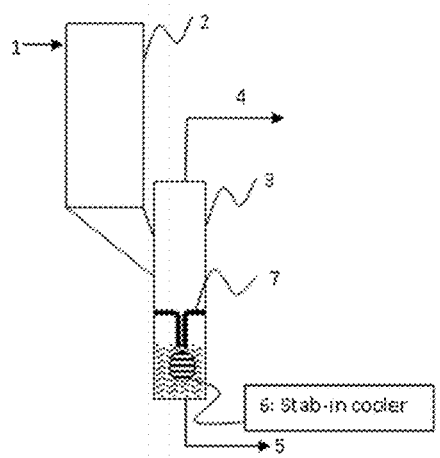
FIG. 3 is a cross-sectional schematic of a vaporizer with an extended divider plate with gas under the plate with curtain plates extending down into liquid layer directing the flow of incoming fluid directly onto the heat exchanger (stab-in cooler in this case).
Figure 4:
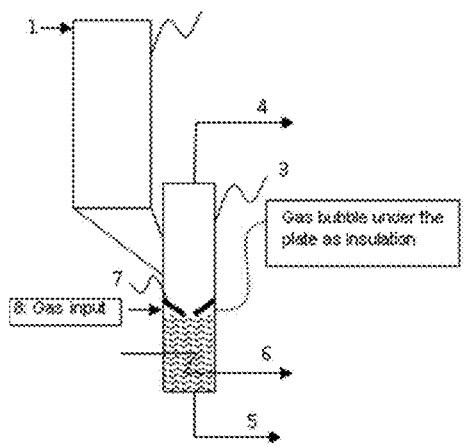
FIG. 4 is a cross-sectional schematic of a vaporizer with a sloped divider plate with gas entrained under the plate with optional small gas input to maintain the entrained gas bubble.

In a preferred embodiment, a simple separator plate, preferably slightly sloping towards one or more perforations that are directly above the heat exchanger (6), is shown in FIG. 4. For example, heat exchanger (6) may be a "stab-in bundle" cooler, in which case the perforation may be a slot directly over and running in parallel, or coaxially, with the length of the "stab-in" cooler. The design shown in FIG. 3 is similar in that there is a sheath or curtain plates extending the vertical liquid flow (and extending the gas bubble zone for enhanced insulation value). The slot is preferably oriented the same as the slot of FIG. 4, and the liquid level is controlled to have the sheath form a gas-liquid seal and the liquid level is maintained above heat exchanger (6). In one embodiment of the invention, the slot or opening above heat exchanger (6) is a first opening, and the plates further define a second opening below the heat exchanger (6), the second opening having the same or greater area as the first opening.

Figure 5A:
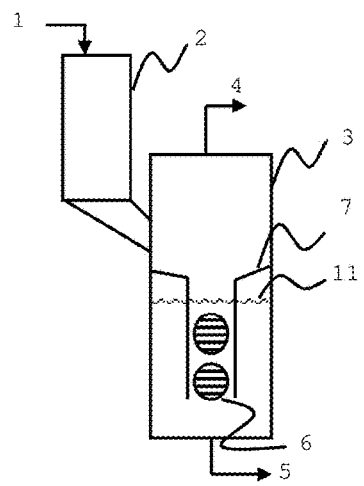
FIGS. 5a-c are cross-sectional schematic of vaporizers having at least one divider plate with extended curtain plates similar to FIG. 3 but with the heat exchanger inside or between the curtain plates. Straight and wrap-around curtain modes are shown.
Figure 5B:
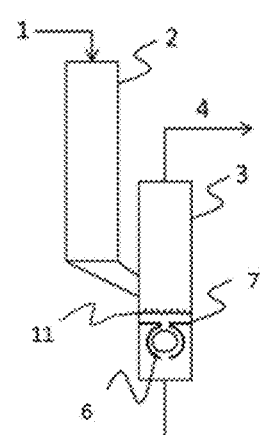
Figure 5C:
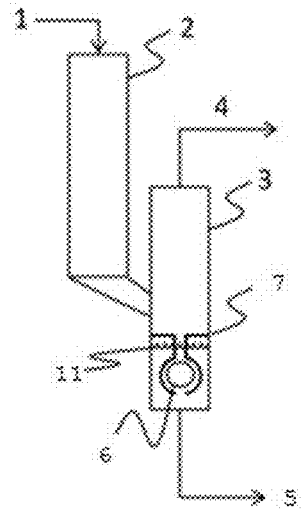

The vaporizers of FIGS. 5a-c are similar in that there is a sheath at least partially enclosing the heat exchanger extending the liquid flow (and extending the gas bubble zone for enhanced insulation value). The slot is preferably directly over and aligned with a "stab-in cooler," the liquid level is controlled to have the sheath forming a gas-liquid seal, and the liquid level is maintained above the cooler. As shown in FIG. 5a, the sheath preferably extends past the heat exchanger(s) and, as shown in FIG. 5b, can partially enclose or wrap around the heat exchanger such that the liquid is guided over the bundle of tubes to enable greater or maximum efficiency of the cooler. FIG. 5c also shows a preferred design with the liquid level (11) below the upper part of the divider plate.

Figures 7A, 7B:
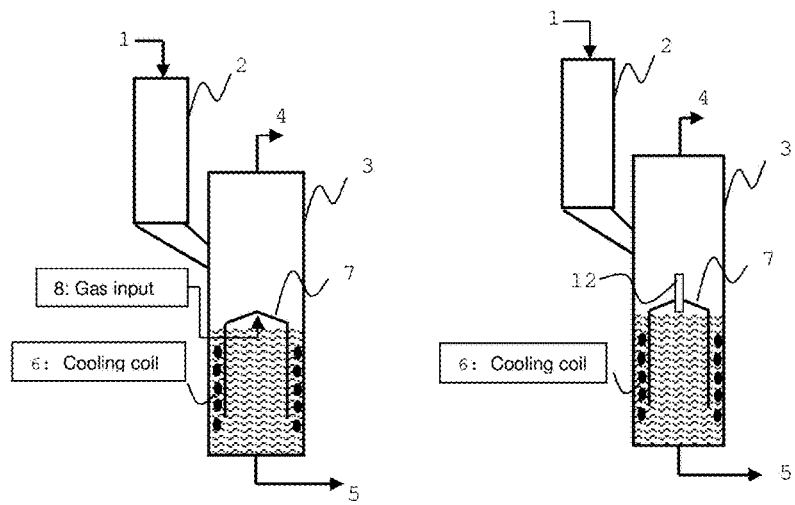
FIGS. 7a and 7b are cross-sectional schematics of a vaporizer with a "cone" style divider plate and extended curtain plates to direct the liquid flow towards cooling coils located around the periphery of the liquid region of the gas-liquid separation zone. An optional gas input (8) is shown in FIG. 7a to maintain a gas bubble under the cone.

In one embodiment, a gas layer is present under the divider plate to add insulation between the layers. This is accomplished either by passive design, e.g., by using a sloped plate and controlling the liquid level close to the gas-liquid seal, or preferably by feeding a small flow of non-condensable gas under the plate. This is shown in FIG. 4 and FIG. 7 as stream (8). The use of the added gas stream (described below) means the liquid level control need not be as accurate as in the passive design.

Figure 6:
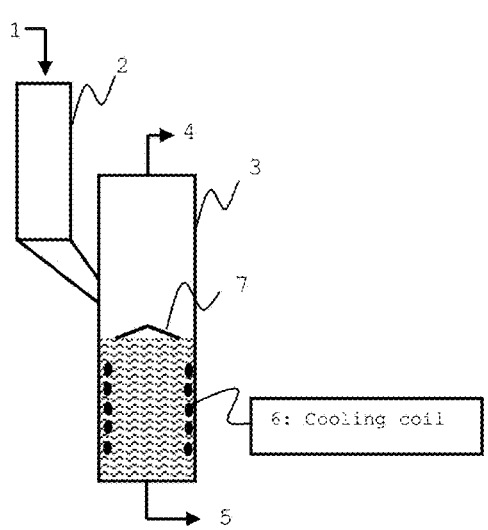
FIG. 6 is a cross-sectional schematic of a vaporizer with a "cone" style divider plate and cooling coils located around the periphery of the liquid region of the gas-liquid separation zone.

With a cooling coil arrangement, the preferred plate would be a slightly coned design with the holes or slots directly over the cooling coils around the perimeter, an example of which is shown in FIG. 6. Even more preferred would be curtain plates down the interior of the liquid layer to enhance the contact time as shown in FIG. 7. These designs direct the hot fluid directly to the cooling medium to expedite the cooling process. An optional gas input stream (8) with an associated bleed hole vent at the gas-liquid interface is used to maintain a gas bubble under the dome for insulation. Alternatively, a chimney (12) can be used to passively control the gas layer under the top of the cone style divider plate.

Any of these designs may be readily retrofitted to an existing gas-liquid separator or easily constructed in a new unit. Optionally, the plate may comprise more than one plate in parallel, or two or more plates in parallel with vacuum or inert gas between them as insulation. Additional optional baffles within the liquid layer to channel flow over the coolers can be used.

Optionally, introducing a non-condensable gas stream (8) under the plates will form a small pocket of gas under the plate (particularly the conical shaped design of FIG. 7) and further adds insulation value to this boundary area. This is particularly advantageous in systems where high vacuum is not used, such as in a stripping gas vaporizer, see, e.g., U.S. Pat. No. 8,404,903. The preferred non-condensable gases include CO and CO-containing streams, such as syngas from the hydroformylation system and reactor vents. The flow is generally very low since it is only necessary to maintain the bubble under the plate. Small perforations in the curtain plates to allow excess gas to escape can be used to maintain the gas level under the cone. With stripped gas vaporizers, a portion of the stripping gas can be diverted for this stream or alternatively the overhead gas stream from a reactor vent condenser can be used.

One mode of operation is to control the liquid level above the highest point of the plate except where gas input is used to generate a gas pocket under the plate. An accurate liquid level control is not critical to the invention as long as (1) the liquid level is above the cooler and (2) at least some of the plate is covered with liquid to give a gas-seal. The use of vent holes, chimneys, or gas-exit slots (not shown) can also be used to control liquid level by allowing free movement of small amounts of liquid and/or gas and maintain the gas seal at the plate. It is important to minimize vapor flow past the plate in order to minimize vapor contact with the cooled liquid and to minimize vapor condensation below the plate.

Any suitable type of vaporizer may be employed. One class of vaporizer includes devices that employ a stripping gas to aid in the separation of the components of the product-containing stream from the product. The vaporizer may be operated under vacuum or at atmospheric or superatmospheric conditions.

The type of vaporizing zone employed in the vaporizer is not critical to the invention and may comprise known conventional designs such as falling film evaporators, thin-film vaporizers, wiped film evaporators, and the like. They are typically vertical tubular heat exchangers whose dimensions (number of tubes, diameter, and length) are determined by plant capacity and vendor's fabrication shop capabilities.

In the process of the invention, the gas-liquid mixture entering the separation zone from the vaporizing zone separates into liquid and gas. The liquid is cooled in the separation zone so that the temperature of the liquid is lower than the temperature of the vapor space. In one embodiment, the liquid temperature is measured at the liquid withdrawal port. The cooling can be accomplished by internal and/or external heat exchangers. Heat exchangers in the bottom portion of the gas-liquid separation zone may be cooling coils, cold-fingers, bayonet or stab-in cooling bundles. External heat exchangers can also be used wherein at least a portion of the cooled liquid is sent back to the liquid region of the separation zone.

An additional advantage of the process of the invention is a cooled supply of feed to a downstream pump (not shown), which will move the material in stream (5) from a low pressure regime (i.e., the vaporizer) to a higher-pressure regime (i.e., the hydroformylation reaction zone). These high speed pumps require constant liquid feed; thus, using the liquid region of the separation zone effectively as a cooled surge tank is advantageous to long pump life. For example, this insures the desired net positive suction head for the pump used to transfer material back to the reaction zone. If suction pressure decreases below vapor pressure due to lack of liquid inventory, some liquid will vaporize, creating bubbles, which will implode in the pump, creating undesired pump cavitation. The inventory of cool material stored in the bottom of the vaporizer acts as an integrated cooled surge tank that minimizes transfer lines, unit footprint, and capital costs.

Advantageously, the product of the process is a $C_3$-$C_{20}$ aldehyde. Illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl 1-heptanal, nonanal, 2-methyl-1-octanal, decanal, adipaldehyde, 2-methylglutaraldehyde, 2-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, 2-methyl 1-decanal, 3-propyl-1-undecanal, pentadecanal, 3-propyl-1-hexadecanal, eicosanal, 2-methyl-1-tricosanal, pentacosanal, 2-methyl-1-tetracosanal, nonacosanal, 2-methyl-1-octacosanal, hentriacontanal, 2-methyl-1-triacontanal, and the like. Illustrative asymmetric optically active aldehyde products include (enantiomeric) aldehyde compounds prepared by the hydroformylation process of this invention such as, e.g., S-2-(p-isobutylphenyl)-propionaldehyde, S-2-(6-methoxy-2-naphthyl)propionaldehyde, S-2-(3-benzoylphenyl)-propionaldehyde, S-2-(3-fluoro-4-phenyl)phenylpropionaldehyde, and S-2-(2-methylacetaldehyde)-5-benzoylthiophene.

SPECIFIC EMBODIMENTS OF THE INVENTION

The following examples are given to illustrate the invention and should not be construed as limiting its scope.

EXAMPLE 1

An ASPEN model of a commercial-scale hydroformylation vaporizer processing 50,175 kg/hr of crude reaction mixture is used to assess the rate of aldehyde trimer removal with the vaporized product stream as a function of vaporizer overhead temperature at 2 bar absolute total pressure. The hydroformylation unit is operated at 90° C. and is found to generate approximately 48 kg/hr of aldehyde trimer.

The composition of the vaporizer feed is given in Table 1 and is based on a typical propylene to butyraldehyde triphenylphosphine-rhodium (TPP-Rh) hydroformylation catalyst. The vaporizer outputs depend on the temperature as shown below.

TABLE 1

Vaporizer Overhead Composition as a Function of Gas-Liquid Separator Zone Temperature as Measured in the Vaporizer Overhead Stream.

| Mass Flow (kg/hr) | VAPORIZER FEED (1) | Vaporizer Overhead Temperature (° C.) | | | | | |
|---|---|---|---|---|---|---|---|
| | | 90 | 95 | 100 | 105 | 110 | 115 |
| | | Vaporizer overhead (4) compositions (kg/hr) | | | | | |
| $H_2$ | 0.032 | 0.032 | 0.032 | 0.032 | 0.032 | 0.032 | 0.032 |
| $N_2$ | 1.095 | 1.087 | 1.091 | 1.093 | 1.094 | 1.095 | 1.095 |
| CO | 0.171 | 0.169 | 0.17 | 0.17 | 0.17 | 0.17 | 0.17 |
| $CH_4$ | 2.4 | 2.3 | 2.4 | 2.4 | 2.4 | 2.4 | 2.4 |
| Propylene | 532 | 445 | 483 | 509 | 520 | 524 | 525 |
| Propane | 990 | 844 | 909 | 952 | 970 | 976 | 980 |
| Isobutanal | 2778 | 573 | 983 | 1605 | 2064 | 2292 | 2416 |
| N-Butanal | 28936 | 4857 | 8705 | 15150 | 20380 | 23099 | 24600 |
| N-Butanol | 8.805 | 0.432 | 0.906 | 2.018 | 3.454 | 4.587 | 5.416 |
| Dimer | 15.95 | 0.29 | 0.61 | 1.43 | 2.69 | 3.97 | 5.16 |
| Trimer | 9961 | 1.35 | 3.29 | 8.85 | 19.71 | 35.50 | 57.23 |
| TPP | 6950 | 0.09 | 0.22 | 0.56 | 1.17 | 1.99 | 3.06 |

Figure 8:
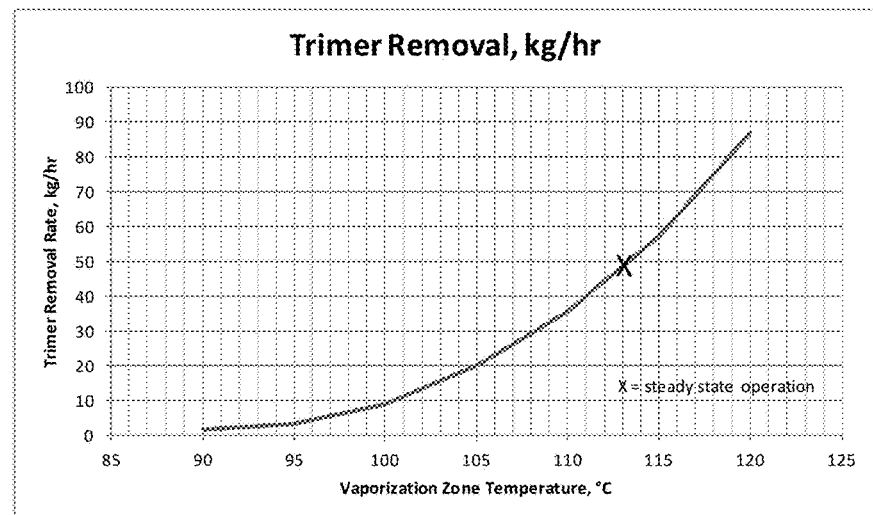
FIG. 8 is a plot of data from Example 1 showing the aldehyde trimer removal rate as a function of the separation zone temperature.

For steady state operation, the vaporizer must remove aldehyde trimer at a rate that is equal to or greater than its formation rate to avoid excessive accumulation of trimers in the reaction zone. FIG. 8 is a plot data from Example 1 showing the aldehyde trimer removal rate as a function of the separation zone temperature. As shown in FIG. 8, the vaporizer temperature preferably is approximately 113° C. to achieve steady state operation. It is also clear that if the bottom liquid of the gas-liquid separation zone is less than 100° C., it acts as a condenser, and an insufficient amount of aldehyde trimer will be removed via the vaporizer overhead stream. Since the bottom liquid has a typical residence time of from 5-10 minutes, maintaining the bottom liquid temperature at 113° C. to avoid condensation increases the rate of ligand decomposition and rate of heavies formation.

The divider plate of the invention is believed to keep the liquid of the separation zone that is above the divider plate relatively hot, yet the bulk of the liquid below relatively cool, achieves both good aldehyde trimer removal and reduces temperature-induced side reactions.

What is claimed is:

1. A process comprising: (a) contacting CO, $H_2$, and at least one olefin under hydroformylation conditions sufficient to form at least one aldehyde product in the presence of a hydroformylation catalyst; (b) removing a product-containing liquid from the reaction zone and sending it to a vaporizer, which comprises a vaporizing zone and a vapor/liquid separation zone, wherein the product-containing liquid, which comprises crude product and catalyst, is heated in the vaporizing zone to form a mixture of gas and catalyst-containing liquid, which mixture is then phase separated in the separation zone, which separation zone has a liquid withdrawal port, a liquid region, a vapor space and a gas-liquid interface, wherein the liquid region comprises at least one divider plate, which optionally contains at least one perforation, wherein at least a portion of at least one divider plate is in proximity to the gas-liquid interface, with the proviso that at least a portion of at least one divider plate is at or below the interface, and wherein the temperature of the catalyst-containing liquid, measured at the liquid withdrawal port, is lower than the temperature of the vapor space.

2. The process of claim 1 wherein at least one plate is perforated.

3. The process of claim 1 wherein at least one plate is sloped to direct the non-volatilized catalyst-containing liquid, towards at least one perforation.

4. The process of claim 1 wherein a heat exchanger controls the temperature of the catalyst-containing liquid in at least a portion of the liquid region.

5. The process of claim 4 wherein the heat exchanger is in the liquid region and wherein at least two plates define an opening directly above the heat exchanger.

6. The process of claim 4 wherein at least one divider plate at least partially encloses the heat exchanger.

7. The process of claim 4 wherein the liquid region contains the heat exchanger, and at least one plate comprises at least one perforation that is directly above the heat exchanger.

8. The process of claim 1 wherein the catalyst comprises a rhodium-phosphorus complex catalyst and the product is a $C_3$-$C_{20}$ aldehyde.

9. The process of claim 1 wherein a non-condensable gas flow is introduced below at least one plate such that a gas bubble or zone is maintained under the plate.

10. The process of claim 1 wherein at least one plate reduces heat transfer between the vapor space and the liquid region.

11. The process of claim 5 wherein the opening above the heat exchanger is a first opening, and the plates further define a second opening below the heat exchanger, the second opening having the same or greater area as the first opening.

* * * * *